(12) United States Patent
Collins et al.

(10) Patent No.: US 10,406,305 B2
(45) Date of Patent: *Sep. 10, 2019

(54) INHALATOR DEVICE AND METHOD

(71) Applicant: John R. Collins, Provo, UT (US)

(72) Inventors: John R. Collins, Provo, UT (US); Ed Dittmar, Coeur d'Alene, ID (US)

(73) Assignee: John R. Collins, Provo, UT (US)

( * ) Notice: Subject to any disclaimer, the term of this patent is extended or adjusted under 35 U.S.C. 154(b) by 339 days.

This patent is subject to a terminal disclaimer.

(21) Appl. No.: 15/370,180

(22) Filed: Dec. 6, 2016

(65) Prior Publication Data

US 2017/0087314 A1 Mar. 30, 2017

Related U.S. Application Data

(63) Continuation of application No. 14/205,106, filed on Mar. 11, 2014, now Pat. No. 9,555,201.

(Continued)

(51) Int. Cl.
*A61M 15/00* (2006.01)
*A61M 16/00* (2006.01)

(52) U.S. Cl.
CPC ...... *A61M 15/0098* (2014.02); *A61M 15/009* (2013.01); *A61M 15/0013* (2014.02);
(Continued)

(58) Field of Classification Search
CPC ............ A61M 15/009; A61M 15/0086; A61M 15/0021; A61M 15/0098;
(Continued)

(56) References Cited

U.S. PATENT DOCUMENTS 5,113,855 A 5/1992 Newhouse
5,201,308 A 4/1993 Newhouse
(Continued)

FOREIGN PATENT DOCUMENTS

EP 2067497 A1 6/2009
GB 1358303 7/1974
(Continued)

OTHER PUBLICATIONS

Boehringer Ingelheim; Boehringer Ingelheim Launches Combivent® Respimat® (ipratropium bromide and albuterol) Inhalation Spray for Chronic Obstructive Pulmonary Disease; press release; Sep. 18, 2012; 3 pages; Boehringer Ingelheim International GmbH.
(Continued)

*Primary Examiner* — Nathan R Price
*Assistant Examiner* — Anh Bui
(74) *Attorney, Agent, or Firm* — Thorpe North & Western LLP

(57) ABSTRACT

A hand-held, portable inhalator device is disclosed. The device has a mouthpiece with a chamber operatively coupled to a medication inlet and a fluid outlet. A valve is disposed about the fluid outlet and is configured to open when subjected to a first threshold level of positive pressure permitting egress of fluid from the chamber. A trigger is configured to dispense medication from a medication source through the medication inlet and into the chamber after a second threshold level of positive pressure is achieved within the chamber of the mouthpiece and maintained for a threshold period of time.

17 Claims, 8 Drawing Sheets

Related U.S. Application Data

(60) Provisional application No. 61/776,330, filed on Mar. 11, 2013.

(52) U.S. Cl.
CPC .... *A61M 15/0018* (2014.02); *A61M 15/0021* (2014.02); *A61M 2016/0027* (2013.01); *A61M 2205/13* (2013.01); *A61M 2205/3331* (2013.01); *A61M 2205/581* (2013.01); *A61M 2205/582* (2013.01); *A61M 2205/583* (2013.01); *A61M 2205/8212* (2013.01)

(58) Field of Classification Search
CPC ........... A61M 15/0091–0096; A61M 15/0013; A61M 15/0018; A61M 15/0016
See application file for complete search history.

(56) References Cited

U.S. PATENT DOCUMENTS

| | | |
|---|---|---|
| 5,284,133 A | 2/1994 | Burns et al. |
| 5,357,946 A | 10/1994 | Kee et al. |
| 5,617,844 A | 4/1997 | King |
| 5,738,087 A | 4/1998 | King |
| 5,826,570 A | 10/1998 | Goodman et al. |
| 6,006,747 A | 12/1999 | Eisele et al. |
| 6,019,100 A | 2/2000 | Alving et al. |
| 6,269,810 B1 | 8/2001 | Brooker et al. |
| 6,308,703 B1 | 10/2001 | Alving et al. |
| 6,412,481 B1 | 7/2002 | Bienvenu et al. |
| 6,494,202 B2 | 12/2002 | Farmer |
| 6,510,846 B1 | 1/2003 | O'Rourke |
| 6,584,969 B2 | 7/2003 | Farmer |
| 6,584,971 B1 | 7/2003 | Denyer et al. |
| 6,659,100 B2 | 12/2003 | O'Rourke |
| 6,705,316 B2 | 3/2004 | Blythe et al. |
| 6,786,216 B2 | 9/2004 | O'Rourke |
| 6,805,118 B2 | 10/2004 | Brooker et al. |
| 7,347,201 B2 | 3/2008 | Djupesland |
| 2002/0026940 A1 | 3/2002 | Brooker et al. |
| 2002/0069870 A1 | 6/2002 | Farmer |
| 2002/0189611 A1 | 12/2002 | Greenwood et al. |
| 2003/0079743 A1 | 5/2003 | Genova et al. |
| 2003/0205227 A1 | 11/2003 | Hodson et al. |
| 2003/0209247 A1 | 11/2003 | O'Rourke |
| 2004/0089299 A1 | 5/2004 | Bonney et al. |
| 2004/0129270 A1 | 7/2004 | Fishman |
| 2004/0237961 A1 | 12/2004 | Snow et al. |
| 2005/0011515 A1 | 1/2005 | Lee et al. |
| 2005/0121024 A1 | 6/2005 | Langford et al. |
| 2007/0157931 A1 | 7/2007 | Parker et al. |
| 2008/0011291 A1 | 1/2008 | Fletcher et al. |
| 2008/0223361 A1 | 9/2008 | Nieuwstad |
| 2009/0025718 A1* | 1/2009 | Denyer ............... A61M 11/005 128/203.14 |
| 2009/0064997 A1 | 3/2009 | Li |
| 2010/0263666 A1 | 10/2010 | Nagata et al. |
| 2014/0230811 A1* | 8/2014 | Von Hollen .......... A61M 11/06 128/200.14 |

FOREIGN PATENT DOCUMENTS

| | | |
|---|---|---|
| GB | 2401795 A | 11/2004 |
| WO | WO 02/068031 A2 | 9/2002 |

OTHER PUBLICATIONS

Boehringer Ingelheim; Combivent® Inhalation Aerosol Prescribing Information; Aug. 2012; 19 pages; Boehringer Ingelheim International GmbH.

Boehringer Ingelheim; FDA Approves Combivent® Respimat® (ipratropium bromide and albuterol) Inhalation Spray for the Treatment of Patients with Chronic Obstructive Pulmonary Disease; press release; Oct. 7, 2011; 3 pages; Boehringer Ingelheim International GmbH.

Boehringer Ingelheim; Prescribing Information for Atrovent® HFA; Aug. 2012; 11 pages; Boehringer Ingelheim International GmbH.

Glaxosmithkline, Inc.; Respiratory Inhaler Identification Chart; poster; Jul. 21, 2005; 1 page; GlaxoSmithKline, Inc.

Hamdan et al.; Positive End-Expiratory Pressure; Posted on Integrating the Healthcare Enterprise website; ftp.ihe.net/Patient_Care_Devices/Profiles/SA/Models/2009-01-07_SemArch_d2/x73NomV2-SemArch-d2/Refs/PEEP_ch225.pdf; Jan. 21, 2009; pp. 815-817;. IHE International, IHE.net.

Hospiscript; Combivent® Respimat® (ipratropium & albuterol) Inhalation Spray for COPD to Replace Combivent® MDI; medication update flyer; Apr. 2013; 1 page; HospiScript Services.

Pollack et al.; Treatment of Acute Bronchospasm With β-Adrenergic Agonist Aerosols Delivered by a Nasal Bilevel Positive Airway Pressure Circuit; Annals of Emergency Medicine; Nov. 1995; pp. 552-557; vol. 26, Issue 5; Mosby Inc./Elsevier.

Soroksky, MD et al.; A Pilot Prospective, Randomized, Placebo-Controlled Trial of Bilevel Positive Airway Pressure in Acute Asthmatic Attack; Chest; Apr. 2003; pp. 1018-1025; vol. 123, No. 4; The American College of Chest Physicians.

Extended European search report dated Mar. 6, 2018, in EP Application No. 17184056.4, filed Mar. 11, 2014; 7 pages.

* cited by examiner

INHALATOR DEVICE AND METHOD

PRIORITY CLAIM

The present application is a continuation of U.S. Ser. No. 14/205,106 filed on Mar. 11, 2014 which claims priority to U.S. Provisional Application 61/776,330 entitled "Inhalator System and Method" filed on Mar. 11, 2013, both of which are incorporated herein by reference in their entirety.

FIELD OF THE INVENTION

The present invention relates to devices for delivery of medication to the airways of a patient and more particularly to delivery mechanisms intended to deliver medication to a patient after the creation of positive end expiratory pressure.

BACKGROUND OF THE INVENTION AND RELATED ART

Patients who suffer from respiratory ailments including chronic obstructive pulmonary disease, asthma, bronchitis, tuberculosis, or other disorder or condition that causes respiratory distress, often self-administer medication to treat symptoms for those ailments.

Presently, many patients attempt delivery of medications to the respiratory system through hand-held metered dose inhalers (MDI) and dry powder inhalers (DPI). Small volume nebulizers (SVN) may also be used. An MDI is a device that helps deliver a specific amount of medication to the lungs, usually by supplying a short burst of aerosolized medicine that is inhaled by the patient. A typical MDI consists of a canister and an actuator (or mouthpiece). The canister itself consists of a metering dose valve with an actuating stem. The medication typically resides within the canister and is made up of the drug, a liquefied gas propellant and, in many cases, stabilizing excipient. Once assembled, the patient then uses the inhaler by pressing down on the top of the canister, with their thumb supporting the lower portion of the actuator. Actuation of the device releases a single metered dose of liquid propellant that contains the medication. Breakup of the volatile propellant into droplets, followed by rapid evaporation of these droplets, results in an aerosol consisting of micrometer-sized medication particles that are then breathed into the lungs. Other MDI's are configured to be charged by twisting a cylinder that charges the device. A button on a side of the cylinder is depressed by the user which results in a timed release of nebulized or aerosolized medication for inhalation by the patient.

DPI's involve micronized powder often packaged in single dose quantities in blisters or gel capsules containing the powdered medication to be drawn into the lungs by the user's own breath. These systems tend to be more expensive than the MDI, and patients with severely compromised lung function, such as occurs during an asthma attack, may find it difficult to generate enough airflow for satisfactory performance.

While used widely for the treatment of respiratory distress, treatment protocols using MDI's and DPI's ignore the physiological state of patients suffering from respiratory distress. That is, generally speaking, many patients presenting symptoms related to respiratory distress suffer from closed or inflamed alveoli. It is the inflammation of the airways within the lungs of the patient that causes discomfort and other symptoms related to their respiratory distress. Unfortunately, common treatment techniques related to MDI and DPI use, deliver medication to inflamed and non-inflamed airways alike. The desired physiological response to the administered medications (i.e., the opening or reduced inflammation of the airways, etc.) is delayed as the medication is absorbed into the bloodstream and thereafter delivered to the closed or inflamed airways. Moreover, use of MDI's or DPI's can be difficult to administer to very young or very old patients or others with decreased or low dexterity. For example, a patient suffering from an acute asthmatic attack may have a difficult time taking a deep enough breathe to move an aerosol from an MDI down through the patient's airway. A need exists, therefore, for improved systems and methods for lung recruitment and more efficient delivery of medication to the lung.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention they are, therefore, not to be considered limiting of its scope. It will be readily appreciated that the components of the present invention, as generally described and illustrated in the figures herein, could be arranged and designed in a wide variety of different configurations. Nonetheless, the invention will be described and explained with additional specificity and detail through the use of the accompanying drawings in which:

DETAILED DESCRIPTION OF EXEMPLARY EMBODIMENTS

Figure 1:
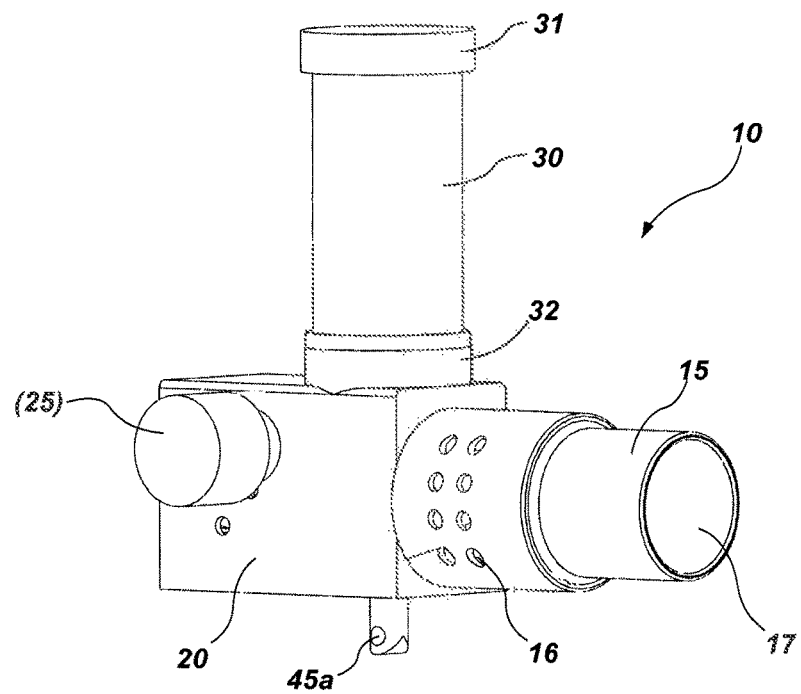
FIG. 1 is a side perspective view of an inhalator device in accordance with one embodiment of the invention.
Figure 2:
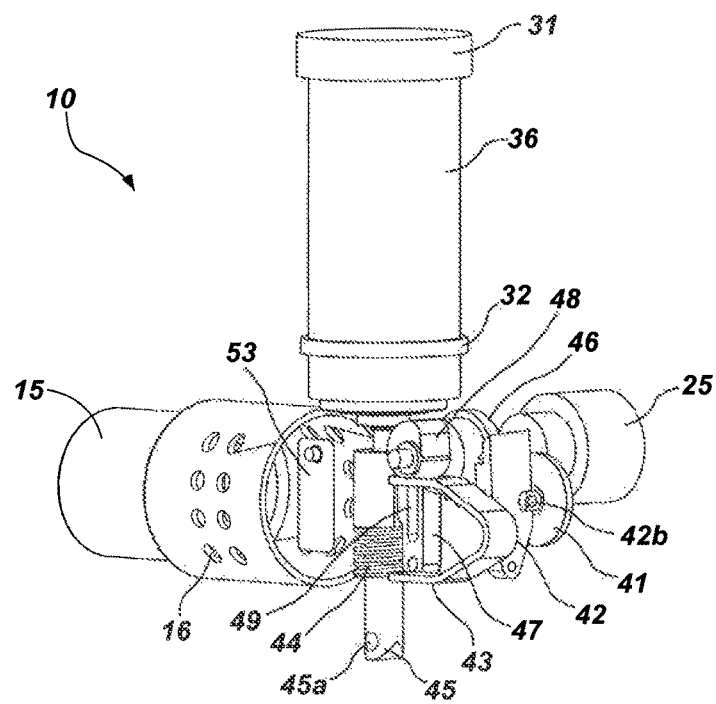
FIG. 2 is a side perspective view of the inhalator device of FIG. 1 with a portion of the housing removed in accordance with one embodiment of the invention showing certain elements contained within the housing.
Figure 3:
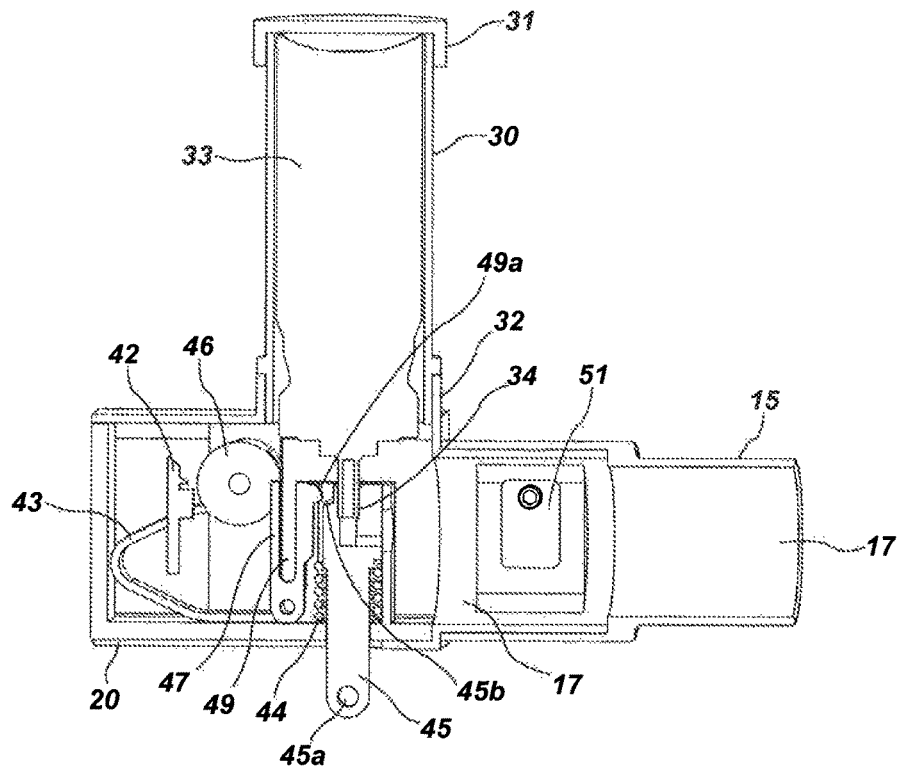
FIG. 3 is a cross-section side view of the inhalator device of FIG. 1 in accordance with one embodiment of the invention showing certain elements contained within the housing.
Figure 4:
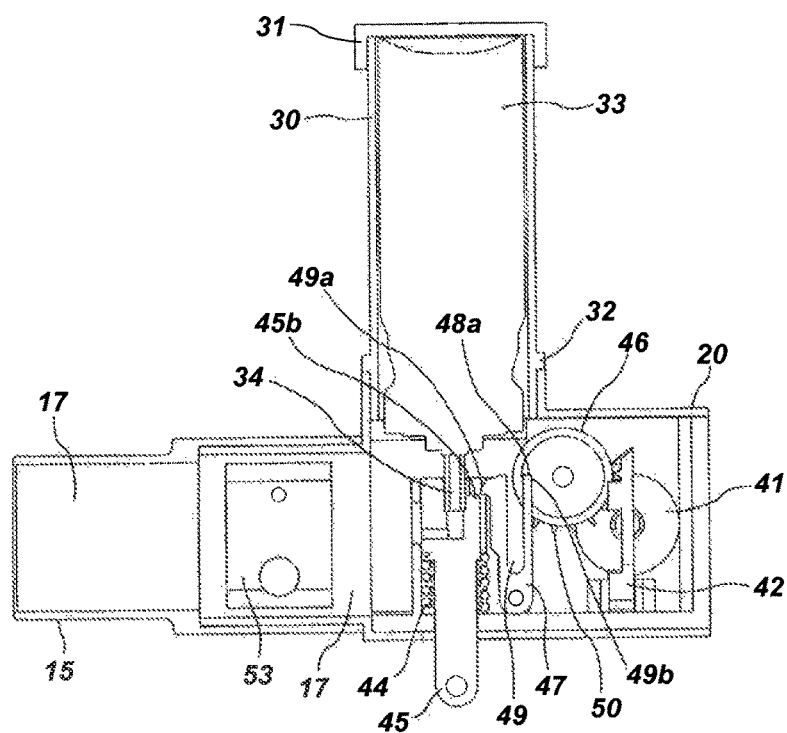
FIG. 4 is a cross-section side view of the inhalator device of FIG. 1, opposite the side view of FIG. 3 in accordance with one embodiment of the invention showing certain elements contained within the housing.

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout. A significant part of the problem encountered in airway-related medical conditions is the reduction in airway diameter accompanying an acute attack. Bronchospasm and its attendant bronchoconstriction prevent adequate gas exchange in the lung, resulting in elevated levels of carbon dioxide and decreased levels of oxygen in arterial blood. This blood gas imbalance results in an increase in the work of breathing, which is burdensome and stressful to a patient who is often in a state of alarm. The relationship between airway caliber to pressure (or work required) to drive air from one end of a tube to another is understood. The Hagen-Poiseuille equation, also known as the Hagen-Poiseuille law, Poiseuille law or Poiseuille equation, is a physical law that describes the pressure drop in a fluid flowing through a long cylindrical pipe. It can be successfully applied to blood flow in capillaries and veins, or to air flow in lung alveoli. It is believed that the Hagen-Poiseuille equation, when applied to compressible fluids such as air, expresses pressure required to maintain volumetric flow as a function of the radius of the airway raised to the $4^{th}$ power. As a result, even slight changes in the radius of an airway results in a significant change in pressure required to maintain the flow of air into the lung.

With reference to asthma, as an example ailment only, the early stage of an attack is a non-homogenous process. Some airways are narrower than others, while others are effectively occluded altogether. When an aerosol, for example, is administered to the passively breathing patient, the aerosol naturally travels preferentially down the airways of greatest diameter. Certain schools of thought in aerosol administration focus primarily on particle size, quantitative deposition, and even dose metering of stimulants such as catecholamine. It is believed that the lung, if recruited to an optimal functional residual capacity (or FRC), will respond more favorably to inhaled therapy. Broadly speaking, it is believed that the optimal amount of air in a lung is present during the end of a normal expiratory phase. The volume of air may be a different percent of total lung capacity depending on the type of lung condition being treated and the methodology applied.

FRC is made of two volumes, the residual volume (RV) which is the part of the lung that never empties and expiratory reserve volume (ERV) which represents the amount of air that can be exhaled after a normal breath has been completed. FRC is generally a measure of airway and alveoli dilation which are the primary mechanisms dictating the work of breathing on a breath-to-breath basis. Narrow airways can be thought of as narrow straws which require a significant amount of pressure in order to move air. Partially open alveoli can be thought of as small balloons that have not been inflated and are small in diameter. It is difficult to get air into a lung with a low FRC. In other instances, such as a severe asthma attack, air is trapped inside a lung with a high FRC. Bronchospasm, with critically narrowed airways allowing air to enter the lung but preventing its escape results in the trapping of air in the lungs.

Lungs with both high and low FRC can be treated with appropriately applied positive end-expiratory pressure (PEEP). Put simply, applying backpressure to an air-trapped lung will allow the lung to exhale more rapidly and completely. Back pressure applied to a poorly recruited lung will allow it to move air more efficiently while the same back pressure applied to an air-trapped lung will allow it to deflate to an optimal FRC. Unfortunately, asthma attacks may occur at locations with no nearby medical facility that could administer positive end-expiratory pressure therapy to relieve suboptimal FRC and its attendant complications. Attacks could also occur near medical facilities with suboptimal treatment options.

The present invention describes an inhalator device primarily designed to permit a patient to self-administer respiratory medication after partial recruitment of a lung or permit a medical practitioner to assist a patient to do the same. As noted above, during a respiratory attack (e.g., acute asthma, etc.) a patient's airway and alveoli can be restricted minimizing the efficient delivery of medication and causing a patient distress. It is believed that lung recruitment (i.e., opening of closed alveoli and/or restricted airways) can be achieved through positive end-expiratory pressure (PEEP) means. PEEP is used in mechanical ventilation to denote the amount of pressure above atmospheric pressure present in the airway at the end of the expiratory cycle. That is, as a patient exhales against a means designed to cause a positive back pressure against the patient's breath, it is believed that partial recruitment of the lung occurs. Thus, PEEP is believed to improve gas exchange by preventing alveolar collapse, recruiting more lung units, increasing functional residual capacity, and redistributing fluid in the alveoli.

It is intended that the inhalator devices of the present invention be operable with different types of functional attachments or components so long as the end result is partial recruitment of a patient's lung prior to dispensation of medication into the inhalator device is achieved. Bearing that in mind, the inhalator devices of the present invention, in accordance with one aspect of the invention, may be described as a hand-held housing having a mouthpiece. The mouthpiece contains apertures for allowing a patient to inhale ambient air and exhale the withdrawn air against a predetermined level of positive pressure. Within the housing, a device for detecting an amount of pressure exerted by the patient during exhalation and the time over which that pressure is exerted is present. Once a threshold level of pressure within the device has been reached over a predetermined time period, a firing mechanism triggers dispensation of medication within the housing permitting the patient to inhale the medication after partial recruitment of the lung. In one aspect of the invention, an indicator device (i.e., audible, visual, and/or tactile device) signals to the patient when a medicated breath should be taken and held. Medication is delivered via the device at the beginning of the inhaled breath to optimize the amount of medication inhaled and the depth of the medication carried down the airway.

Another indicator is present providing notice to the patient that he or she may release the breath after a certain period of time.

Example Inhalator #1

The present invention is intended to be operable with numerous inhalator configurations. Specific reference is made herein to a particular configuration of a mechanical inhalator device requiring no external source of power, other than the pressure generated by the patient by way of his or her exhalation. However, it is understood that any inhalator device is contemplated for use herein comprising a device for dispensing a medication once a predetermined level of pressure is detected within the device over a predetermined period of time. Although a mechanical device is more particularly set forth in this embodiment, examples of other devices of inhalators include, but are not limited to, electro-mechanical, electrical, chemo-electrical, and chemo-mechanical embodiments.

Referring now specifically to the figures, in one exemplary embodiment, with reference to FIGS. 1 through 4, a mechanical inhalator device is shown 10. The inhalator device 10 has a mouthpiece 15 on a front end of housing 20. The mouthpiece 15 may have a circular end, as shown in the exemplary embodiment, or any other shape (i.e., oval, rectangular, etc.) as suits a particular purpose. A medical cartridge housing (shown at 30 and 32) contains a medical cartridge 33. The medical cartridge 33 contains any type of medication desired to be delivered to the patient (e.g., Albuterol). A cap 31 encloses the medical cartridge 33 within the housing 30 and 32. The medical cartridge 33 comprises a stem valve 34 that dispenses a predetermined quantity of medication once the stem valve 34 is pushed upward against the medical cartridge 33. The stem valve 34 is in fluid communication with a chamber 17 within the mouthpiece 15. The term "fluid" is used herein to denote a substance that has no fixed shape and yields easily to external pressure such as a gas (i.e., a compressible fluid) or a liquid (i.e., a non-compressible fluid). Importantly, the medical cartridge 33 is disposed within housing 30 and 32 such that in the event of mechanical failure of the device 10, a patient may manually actuate stem valve 34 thereby releasing an administering dose of medication.

The mouthpiece 15 comprises a plurality of inhalation apertures 16 disposed about the outer periphery. The apertures 16 are in fluid communication with chamber 17. The apertures 16 within the mouthpiece 15 permit a user of the device 10 to keep their mouth on the device 10 during the entire cycle of device use. That is, a patient may place his or her mouth over the mouthpiece 15 and draw in breath through the apertures 16. The patient then exhales with his or her mouth still firmly placed on the mouthpiece 15. A flapper check valve 53 within the mouth piece 15 closes off at least some of the apertures 16 creating back pressure against patient's exhalation. A one-way valve or PEEP valve 51 is disposed within the mouth piece 15 permitting a pre-determined quantity of air to escape the mouthpiece 15 once a threshold level of positive pressure pre-determined by the physician in the range of the 3 cm to 20 cm H2O is reached. The quantity of air that may escape and at what threshold pressure it may escape is a function of the size and configuration of the PEEP valve 51. Each exhalation breath that reaches the threshold pressure for the required period of time is considered to be a "qualifying breath."

The housing 20 and mouthpiece 15 are constructed of rigid or semi-rigid plastic material or other suitable composite material suitable for use as a medical device to be placed in the mouth of a patient. For example, Delrin (manufactured by Dupont) or medical-grade acetyl may be used. Similarly, the PEEP valve is constructed from rigid or semi-rigid material, such as urethane, or other suitable material, including metal components, alloys or other composite materials. Plastic components may be injection molded, press molded, printed from a three-dimensional printer, or constructed using any other manufacturing process as is known in the art.

Once the required number of qualifying breaths has been achieved, a device 10 actuates the stem valve 34 which dispenses medication into the chamber 17. In one embodiment, the chamber 17 extends from the front opening of the mouthpiece 15 to the rear of the mouthpiece 15 without a change in the inner volume of the chamber 17. In another embodiment, the volume of the chamber 17 may be larger near the back end of the mouthpiece 15 and smaller near the front end of the mouthpiece 15, or vice versa. In any event, the stem valve 34 is in fluid communication with the chamber 17. In one embodiment of the invention, the device 10 which actuates the stem valve 34 comprises spring-loaded firing piston 45 positioned directly beneath the stem valve 34. While the stem valve 34 and firing piston 45 are shown in a vertical orientation, it is understood that the stem valve 34 and firing piston 45 may also be horizontal or on an inclined plane as suits a particular orientation suited to the dispensing of the medication, so long as the firing piston 45 is configured to push the stem valve 34 into an actuated position or, in one aspect of the invention, the medical cartridge 33 is pushed downward while the stem valve 34 remains stationary. In any event, the stem valve 34 is actuated dispensing a volume of medication.

In one embodiment of the invention, the firing piston 45 is disposed within a spring member 44. Spring member 44 is biased in an unloaded state that, when activated, will push the firing piston 45 upward against the stem valve 34 such that the stem valve 34 is also actuated. A lanyard or cord may be attached to an aperture 45a in the firing piston 45. The lanyard is used to pull the firing piston 45 downward and place the firing piston 45 in a charged or loaded state. Trigger lever 49 has a lip 49a configured to mate with an opposing ledge 45b disposed on an upper level of the firing piston 45. When placed in a loaded state, the lip 49a engages ledge 45b and holds the firing piston 45 in its charged or loaded state. When the trigger lever 49 is actuated, the lip 49a is moved away from the ledge 45b which allows the firing piston 45 to be forced by spring member 44 up against the stem valve 34 thereby actuating stem valve 34 and dispensing a volume of medication.

The trigger lever 49 is controlled by a cam 48 which in turn is rotated by a pressure sensing and timing device. This device comprises an exhale-actuated piston 41 in fluid communication with chamber 17 of the mouthpiece 15. In one embodiment, the piston 41 is located within the housing 20 opposite the mouthpiece 15 and behind the firing piston 45. When a patient blows through the mouthpiece 15 and creates a predetermined level of pressure for a predetermined period of time, the exhale-actuated piston 41 moves shuttle 42 via the connecting rod 42b in a manner that advances the timing gear 46 one position on the timing teeth 50. On the following inhale breath, the piston 41 is returned to its initial position which in turn actuates the shuttle 42 and advances the timing gear 46 to the next ready position.

In accordance with one embodiment of the invention, a user dials in the number of qualifying breaths required to dispense medication by rotating the dial 25 to a desired number indicated on the exterior of the device 10. The number of breaths that may be set to be taken is a function of the number of teeth 50 on the timing gear 46. This action presets the trigger cam 48 to the arming position. The trigger cam 48 holds the firing piston 45 until rotated to the final position at which time the firing piston 45 is released. In one aspect of the invention, the trigger cam 48 is one component of a cam and gear cluster. Other components include a timing gear 46 having twelve or more teeth 50. The twelve teeth comprise six release teeth and six ready teeth positioned in two rows. Additionally, the cam and gear cluster may comprise an advancement cam 48 biased by spring 43. Spring 43 causes the cluster to rotate as the gear teeth 50 are released one notch at a time by movement of the shuttle 42.

In one embodiment of the invention, the user arms the device 10 by pulling the firing piston 45 into the armed position using a lanyard (or other device) disposed through aperture 45a. The spring 43 is biased to the armed position and captured by the trigger lever 49 which is biased by the trigger cam 48 to hold the firing piston 45 in place. The user then places his or her mouth over the mouthpiece 15 and begins breathing through the device 10. In one embodiment of the invention, the first exhale breath from the user causes the piston 41 to move in the cylinder. The piston 41, which is in fluid communication with chamber 17 and connected to a shuttle 42 by connecting rod 42b, moves shuttle 42 to the right releasing the rotation of the gear and cam cluster by one release tooth 50. The following inhaled breath moves the piston 41 connecting rod 42b and shuttle 42 to the left releasing the gear and cam cluster to rotate again by one tooth 50 into the next ready position. These actions are repeated on each inhale and exhale breath until the number of qualifying breaths has been reached and the final breath is taken. Coincident with the final breath, the trigger cam 48 releases the firing piston 45. The medication is then injected into the chamber 17 and the user holds in the final breath for the prescribed period of time (e.g., 3 to 5 seconds).

As noted above, a spring 43 biases cam 48 to rotate and is operatively connected to timing gear 46. Cam member 48 comprises a lip 48a mated with an edge 49b of the trigger lever 49. Once the timing gear 46 is advanced a predetermined level of tooth positions, the cam member 48 is positioned such that a lip 48a of cam member 48 engages with the edge 49b of the trigger lever 49 pulling the trigger lever 49 back. In one aspect of the invention, a predetermined level of pressure required to move piston 41 (i.e., the amount of pressure the patient must maintain within the chamber 17) ranges from 2.0 cm to 6.0 cm H2O. A predetermined level of time (i.e., the time that a patient is required to maintain a predetermined amount of pressure within the chamber 17 of the inhalator 10) ranges from 0.5 to 3.0 seconds. Different ranges of pressure and time are contemplated herein as suits a particular application or prescription from a medical service provider.

In one aspect of the invention, a qualifying breath indicator is disposed within a portion of the housing 20 and operably connected to the firing piston 45. In one embodiment, the breath indicator comprises a piston that is at least partially ejected to the outside of the housing 20 upon, or just prior to (e.g., 1 second before) actuation of the firing piston 45. In this manner, the user is provided with a visual indicator that the firing piston 45 is being actuated and medicine is being dispensed for inhalation. In one aspect, the distal end of the breath indicator piston is colored green so the user observes a green piston exiting from the housing 20. In another embodiment, the breath indicator comprises a metal member that is configured to resonate upon actuation of the firing piston 45. The resonating sound acts as an audible indicator to the patient that medicine is being dispensed for inhalation. However, a breath indicator by any or numerous means may be used as suits a particular application.

Example Inhalator #2

Figure 5:
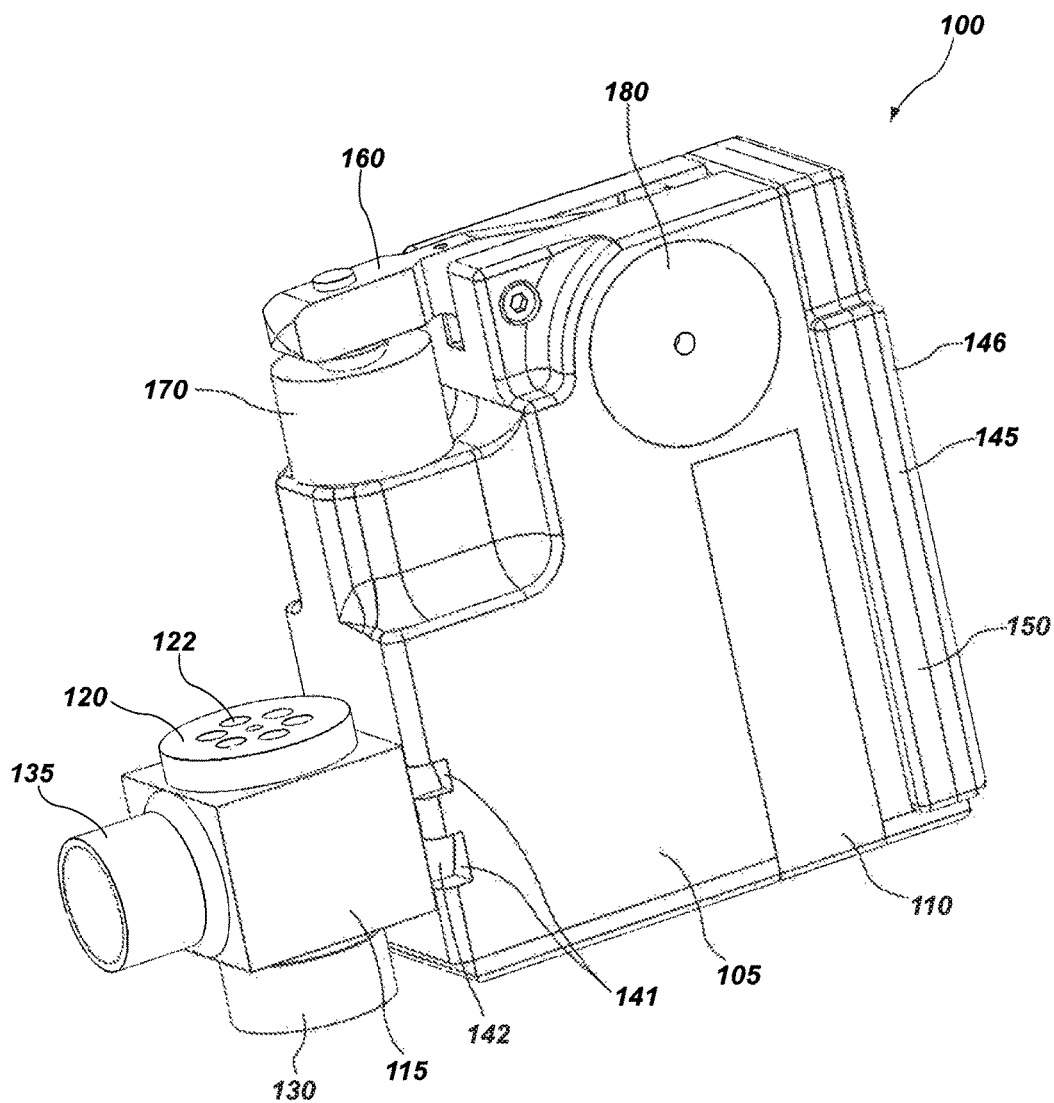
FIG. 5 is a perspective view of an inhalator device in accordance with one embodiment of the invention.
Figure 6:
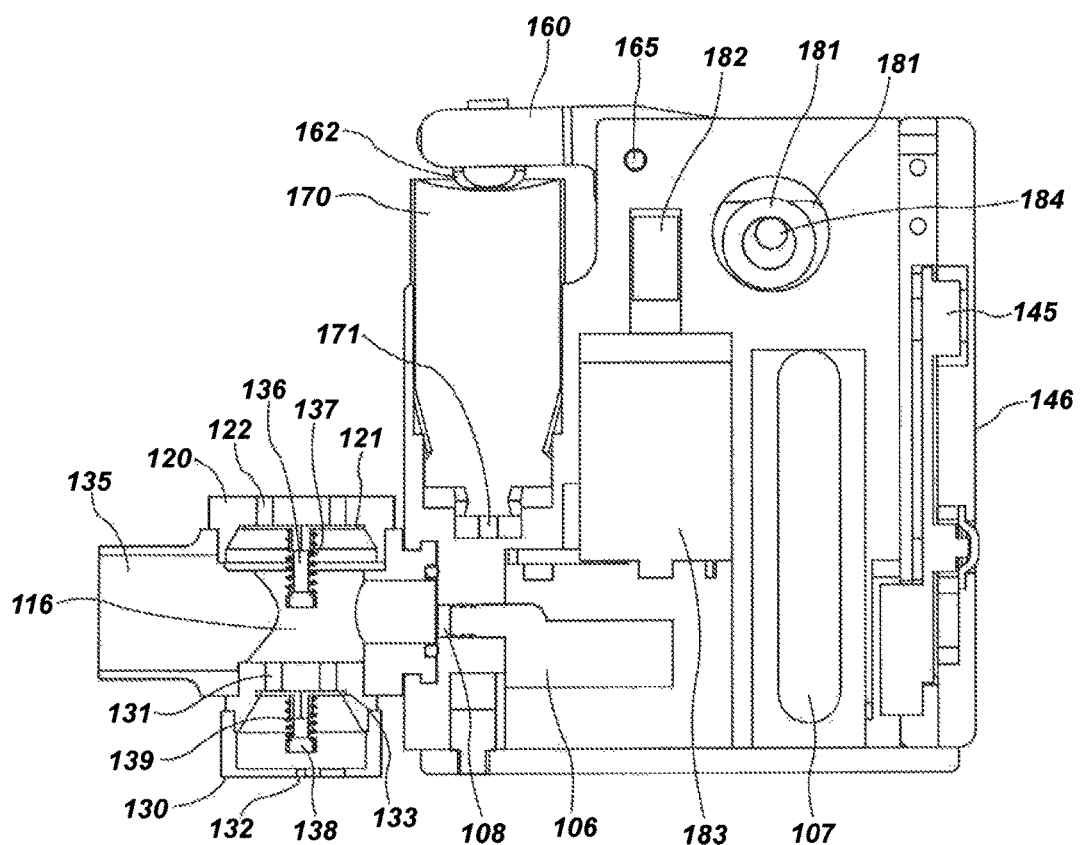
FIG. 6 is a cross-section side view of the inhalator device of FIG. 5 in accordance with one embodiment of the invention.
Figure 7:
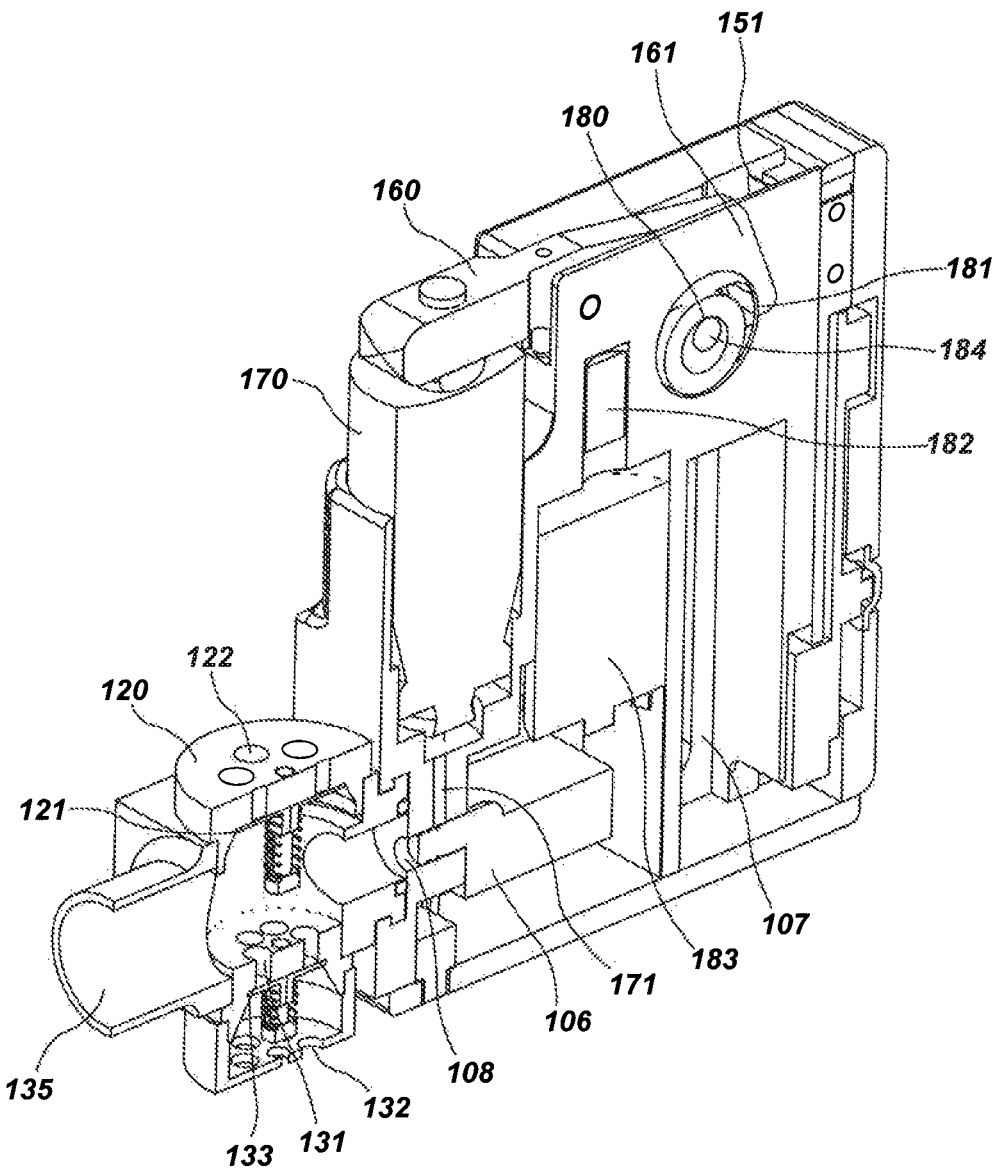
FIG. 7 is a cross-section perspective view of the inhalator device of FIG. 5 in accordance with one embodiment of the invention.
Figure 8:
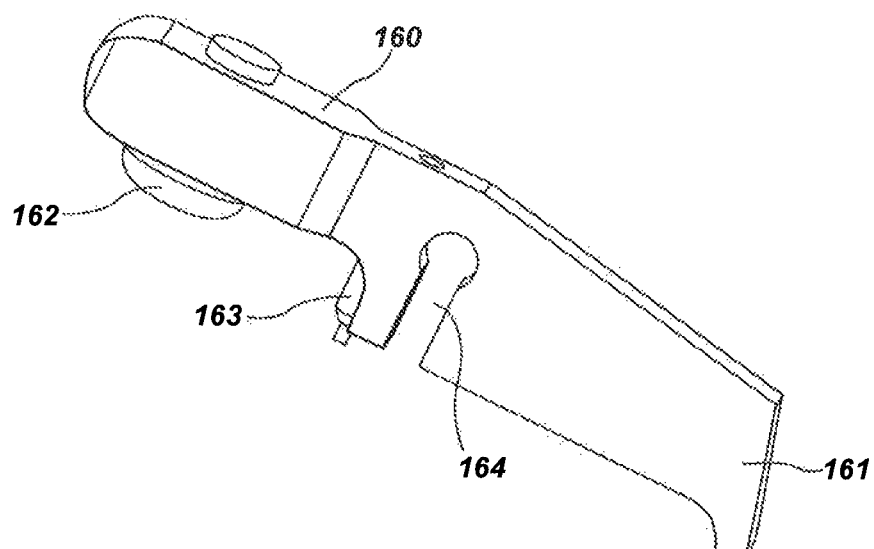
FIG. 8 is a perspective view of an actuating lever of the inhalator device of FIG. 5 in accordance with one embodiment of the invention.
Figure 9:
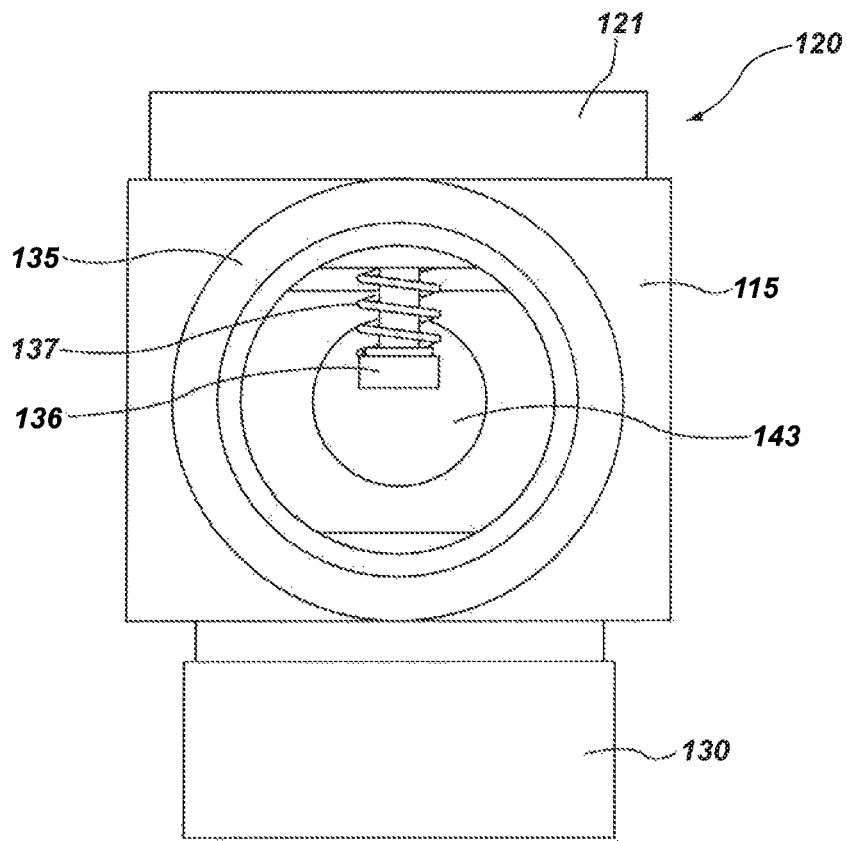
FIG. 9 is a front view of a mouthpiece of the inhalator device of FIG. 5 in accordance with one embodiment of the invention.

In one embodiment of the present invention, an electro-mechanical inhalator device 100 is shown. Broadly speaking, the device 100 relies on principles similar to those described above, but accomplishes the end result through use of electro-mechanical means. Referring now to FIGS. 5-7 generally, an inhalator device 100 is shown in accordance with one embodiment of the invention. The device 100 comprises an outer housing or main body 105 having a battery compartment 110. A removable mouthpiece 115 is disposed on a front end of the housing 105. A worm gear assembly 180 is disposed about a top, rear portion of the housing 105 next to an actuating lever 160. The actuating lever 160 is operatively connected to medication cartridge 170. At the rear of the device 100, a circuit board 145 is operatively connected to the device 100 for the operational sequence and trigger actuating lever 160. The circuit board base 150 is connected to the rear of housing 105.

The mouthpiece 115 comprises a primary chamber 116 with an inhale valve 120 disposed on a top portion of primary chamber 116. The inhale valve 120 comprises a plurality of apertures 122 leading from a top portion of the inhale valve 120 to a moveable plate 121. Plate 121 is disposed atop an adjustable post 136 with a spring member 137 biasing the plate 121 against the bottom of apertures 122. In this manner, the inhale valve 120 is biased in a normally closed position and is opened when negative pressure is induced within the primary chamber 116 of mouthpiece 115. In other words, the plate 121 of inhale valve 120 is moved downward when a user of the inhalator inhales sufficiently to overcome the tension of spring 137. The mouthpiece 115 also comprises a cylinder 135 configured to be inserted within the mouth of a patient. The bottom of the mouthpiece 115 comprises a valve shown generally at 130. In one aspect of the invention, though not in every aspect, the valve 130 is a PEEP valve having a plurality of inner apertures 131 on an inside of the mouthpiece 115 and atop the valve 130 and a plurality of outer apertures 132 on the outside of the mouthpiece 115 and on a bottom of the valve 130. A plate 133 is disposed atop an adjustable rod 138 and spring 139 assembly much like the inhale valve on the top of the mouthpiece 115. In contrast to the inhale valve 120, the plate 133 of the PEEP valve opens when the primary chamber 116 of the mouthpiece 115 experiences positive pressure. That is, when the user blows on the mouthpiece 115, plate 133 is directed downward against spring member 139 opening a passage between upper apertures 131 and lower apertures 132. The tension of spring member 139 may be selected in order to predetermine the quantity of pressure required to move the plate 133 downward sufficient to allow the passage of air. Both rods in the upper and lower valves may be threaded into a portion of the valve and therefore have an adjustable length. In this manner, the tension of the springs 137 and 139 may be adjusted. In one aspect of the invention, the valve 130 opens when subject to a positive pressure pre-determined by medical personnel in the range of 3 cm to 20 cm H2O and the valve 120 opens when subject to a negative pressure of not greater than 0.3 cm H2O.

The mouthpiece 115 is detachably mounted to body 105 through a plurality of grooves 141 disposed within the housing and mating lips 142 disposed within the mouthpiece 115. The grooves 106 are placed horizontally across a front face of the body 105. Mating lips 142 are likely placed horizontally across a back face of the mouthpiece 115. The mouthpiece 115 is mounted and/or removed from the body 105 by sliding the mating lips 142 horizontally through grooves 141 until the inlet 108 of the body 105 is substantially aligned with back outlet 143 of the mouthpiece 115. The groove and lip combination, however, may be arranged vertically or in an inclined plane as suits a particular design. An arrangement of circular grooves and mating lips is also contemplated for use. In this manner, the mouthpiece 115 is attached and/or detached from the body 105 of the device 100 by twisting the groove/lip mating pair into locking engagement. Other attachment means may also be used as suits a particular application and design.

A cavity is formed in the top of the body 105 configured to receive medicine cartridge 170 therein. In one aspect of the invention, medicine cartridge 170 comprises a cylindrical container with pressurized fluids therein. As with other medicine cartridges known in the art, the distal end of the cartridge comprises a stem valve 171 which, when compressed, dispenses a predetermined volume of medicine from the valve 171. The stem valve 171 is in fluid communication with inlet 108 and, once connected to the mouthpiece 115, is also in fluid communication with primary chamber 116 of mouthpiece 115.

Inlet 108 of the body 105 is in fluid communication with pressure sensor 106. When a patient blows on the mouthpiece 115, the upper valve 120 closes and the lower PEEP valve 130 opens. Depending on the tension of spring 139 and the volume of air exhaled by the patient, an amount of positive pressure within the primary chamber 116 is created. Pressure sensor 106 is configured to detect the pressure within primary chamber 116 and the amount of time pressure is continuously maintained. The pressure sensor 106 is configured to relay a signal to circuit board 145 when a qualifying breath has been achieved. Pressure sensor 106 is configured with tolerances to relay signals when a pressure that is within a predetermined (or threshold) for the predetermined (or threshold) period of time. In one embodiment the threshold pressure ranges from between 2 cm and 4 cm H2O and the threshold period of time ranges from between 2 and 6 seconds.

As noted above, a qualifying breath is achieved when a patient blows through the mouthpiece 115 and creates a predetermined (or threshold) level of pressure for a predetermined (or threshold) period of time. In one aspect of the invention, the pressure sensor 106 is configured to be biased in an open or "detecting" configuration. The pressure sensor 106 closes upon detecting approximately 3 cm of H2O and re-opens upon detecting that pressure is less than 1 cm of H2O. Other pressure sensor configurations are contemplated herein. In one aspect of the invention, a qualifying breath is achieved only after the patient maintains the predetermined threshold of pressure within the mouthpiece 115 for the predetermined period of time and the pressure sensor 106 detects a decrease in the pressure within the mouthpiece 115. The decrease in pressure indicates that the patient is no longer blowing into the mouthpiece 115 and is preparing to take another breath. In this manner, if the required number of qualifying breaths has been achieved, medication can be dispensed just prior to an inhalation event. Advantageously, the timing of the dispensing of the medication at the end of an exhalation cycle and just prior to an inhalation event permits the maximum inhalation of medicine into the patients lungs as medicine is drawn into the lungs at the beginning of an inhalation event (i.e., at the point of highest intake of air into the lungs). In one aspect of the invention, a qualifying breath is not achieved until after the patient maintains the predetermined threshold of pressure (e.g., between 2.8 cm and 3.2 cm of H2O) within the mouthpiece for the predetermined period of time (e.g., between 3 and 5 seconds) and the pressure sensor 106 detects a decrease in the pressure within the mouthpiece 115 to below 1 cm H2O. However, in one aspect of the invention, the pressure within the chamber on the exhalation cycle can range from between 0 and 1.5 cm H2O. Other pressures, including those on the end portion of an exhalation cycle, re contemplated herein as suits a particular application.

The pressure sensor 106 and circuit board 145 are operably connected to power source 107. In one aspect of the invention, the power source 107 is a portable power source such as a battery, rechargeable battery or the like. In yet another aspect, the entire device may be tethered to a non-portable energy source. The power source 107 and circuit board 145 are coupled to a motor 183. Once the predetermined number of qualifying breaths has been detected by the circuit board 145, the motor 183 actuates the worm 182 which in turn rotates the worm gear assembly 180. The worm gear assembly 180 comprises a worm gear and an eccentric bearing 181 disposed about a central axis 184. The worm gear assembly 180 is disposed beneath the back of actuating lever 160. When the worm assembly 180 is activated, worm 182 rotates axis 184 until the bearings 181 turn from a first position to a second position. The first bearing position is configured such that the rear 161 of the actuating lever 160 is in a downward position. The second bearing position is configured such that the rear 161 of the actuating lever 160 is in an upward position. In one aspect of the invention, the actuating lever 160 comprises a pivot pin slot 164 where the lever is mounted to the top of the housing 105. A pivot member is disposed through an aperture in the housing 105 and through the pivot pin slot 164. Actuating lever 160 also comprises an adjusting screw 162 configured to rest on top of medicine cartridge 170. When the rear 161 of actuating lever 160 is driven upward by the worm gear assembly 180, the lever 160 pivots about the pivot, driving the front of the lever 160 downward. The downward thrust of the front end of lever 160 drives the medicine cartridge 170 downward and actuates stem valve 171 releasing a dose of medicine.

A return spring cartridge 163 is disposed beneath the lever 160 near the pivot slot 164. The return spring cartridge 163 is configured to bias the rear of the lever 160 in a downward position. In this manner, after the worm gear assembly 180 drives the rear 161 of the actuating lever 160 upward, the return spring cartridge 163 will push the rear end 161 back down to compensate for a slow return of the medication cartridge 170 return action. The actuating lever 160 is designed such that the rear 161 of the actuating lever 160 comes into contact with switch 151 after stem valve 171 is actuated. When actuated, switch 151 closes a circuit sending a current to the motor 183 (thereby operating the worm assembly 180) until the lever 160 returns to a position where switch 151 is disengaged (i.e., lever is in a downward position). This terminates the circuit and its attendant current to the motor 183 ending operation of the worm gear assembly 180. In this manner, the worm gear assembly 180 and lever 160 are returned to a "pre-firing" state readying the device 100 for its next use.

Circuit board 145 is covered by a board cover 146 and is mounted to a base 150. The circuit board 145 is a printed circuit board, or PCB, used to mechanically support and electrically connect electronic components using conductive pathways, tracks or signal traces etched from copper sheets laminated onto a non-conductive substrate, but may comprise any circuit board known in the art capable of carrying out the logic described herein. In one aspect of the invention, the circuit board comprises a PLC circuit or programmable logic controller circuit. A PLC may include a sequential relay control, motion control, process control, distributed control systems, and/or networking as is known in the art. In other aspects of the invention, PLRs (programmable logic relays) may be used. PLR products such as PICO Controller, NANO PLC, and others known in the art are contemplated for use herein. In one aspect of the invention, the circuit board 145 has a memory storage component capable of storing information related to the number of times the device has been fired as the result of the user having achieved the required number of qualifying breaths. In one aspect of the invention, the circuit board 145 includes a data port which may be operably connected to a computer terminal. In this manner, the circuit board logic may be programmed to adjust the number of qualifying breaths required to actuate the actuation lever 160. A computer readable software program capable of operating on any computer operating system known in the art is configured to communicate with the circuit board 145 via a physical connection with the computer system. However, the data may also be relayed to the computer operating system via a wireless signal.

A plurality of LED's are mounted to the circuit board 145 and aligned along an edge of the housing 105 of the device 100 to be visible through the mounting base 150. In one aspect of the invention, the lights all turn on when a user picks up the inhalator 100 or creates a minimum amount of pressure within the primary chamber 116 via an initializing breath. For each qualifying breath thereafter, one of the plurality of lights is extinguished. When the last light is extinguished a green light appears indicating to the user that medication is going to be administered and that the patient should inhale the medication and hold the breath until the green light turns off. In one aspect of the invention, the appearance of the green light is coincident to the actuation of lever 160. In an additional aspect of the invention, the patient hears an audible tone also indicating that medication is going to be administered and that the patient should inhale the medicine. The timing and sequence of the lighting and/or sound, however, are adjustable as suits a particular application. For example, a single yellow light can appear for each qualifying breath leading to a final green light. In other words, for each exhalation event that reaches the predetermined pressure for the predetermined quantity of time, a yellow light appears. Once the required number of yellow lights is established, a green light appears and medication is administered. The sequence and timing are adjustable via a connection to a computer terminal or PLC controls or individual control switches mounted directly to the circuit board 145.

Other sequences or visual and/or audible indicators of the administration of medication are contemplated for use herein. For example, in one embodiment of the invention the pressure sensor 106 is configured to transmit a signal to the circuit board 145 when a first threshold of pressure is detected and when a subsequent lower threshold of pressure is detected. In this manner, an inference may be made generally when the user has ceased blowing on the inhalator 100. The first threshold pressure (i.e., for transmitting the signal) may be from 3 cm to 10 cm H2O and the second lower threshold pressure (i.e., indicating a breath has terminated) may be from 0.5 cm to 1 cm H2O, though other pressure ranges may be used. In one aspect of the invention, the motor 183 will not actuate the worm gear assembly 180 and subsequently administer medication to the patient until after the predetermined number of qualifying breaths has been achieved and after the user has ceased blowing on the inhalator 100.

In yet another aspect of the invention, a tactile sensor is placed on the cylinder 135 of mouthpiece 115. The tactile sensor is operably connected to the circuit board 145 and is designed to send a signal to the circuit board 145 when placed into contact with the skin of a patient. In one embodiment, the circuit board 145 is configured to place the inhalator 100 into "sleep mode" to preserve battery power until the tactile sensor is actuated. In another embodiment, the circuit board 145 is configured to provide an audible, visual, and/or tactile signal to the user as a reminder that the user should keep his or her mouth on the cylinder 135 during the entire exhalation and inhalation process. In other words, once the tactile sensor is actuated, a signal is provided to the user if contact with the tactile sensor is terminated prior to the actuation of the firing piston. In yet another embodiment, if contact with the tactile sensor is terminated prior to actuation of the firing piston, the circuit board 145 is configured to prevent actuation of the piston despite having detected the predetermined number of qualifying breaths. In this manner, medication will only be discharged if the number of qualifying breaths has been achieved, the user has ceased blowing on the device 100, and contact between the skin of the user and the mouthpiece 115 is maintained.

Figure 10:
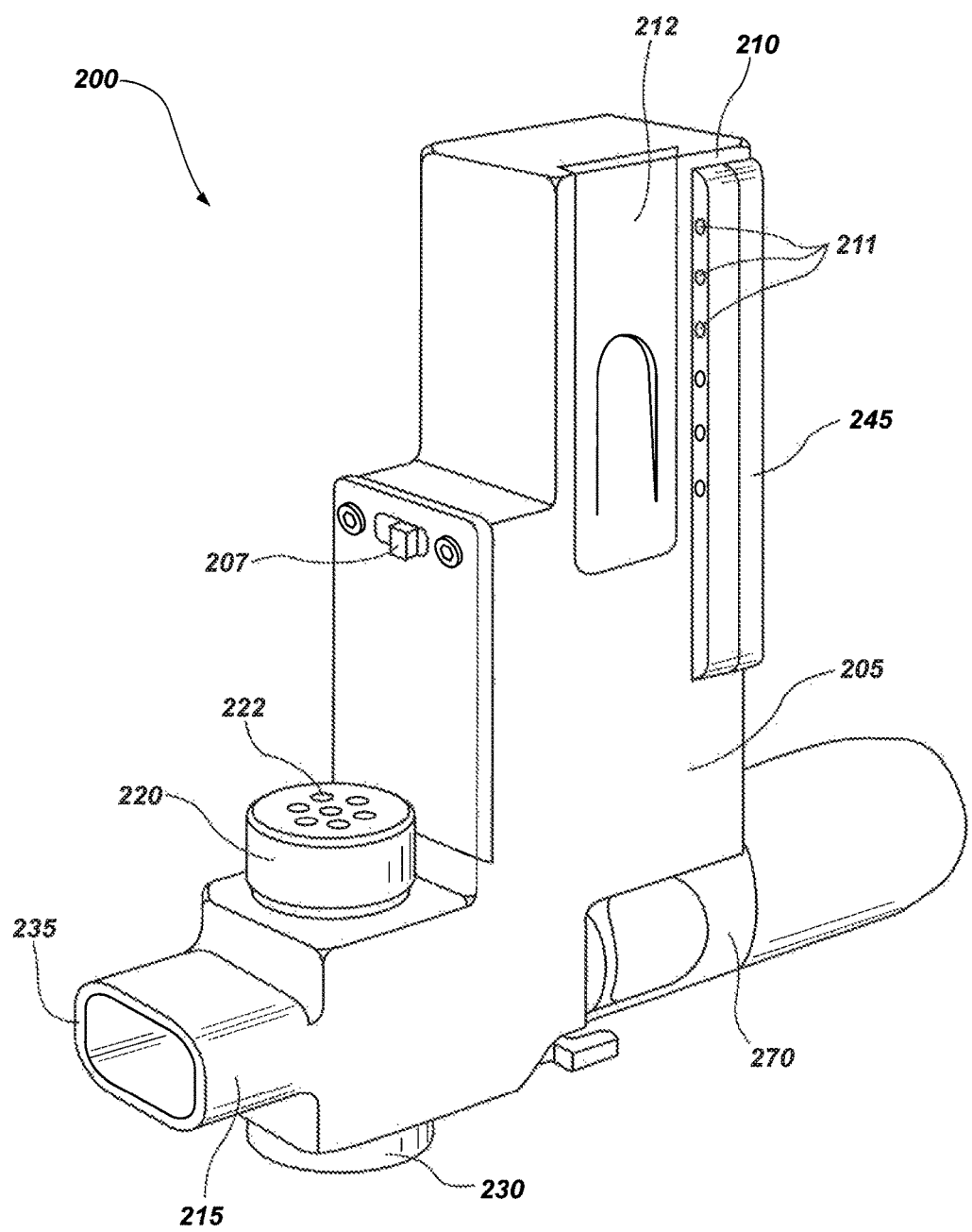
FIG. 10 is a front perspective view of an inhalator device in accordance with one embodiment of the invention.
Figure 11:
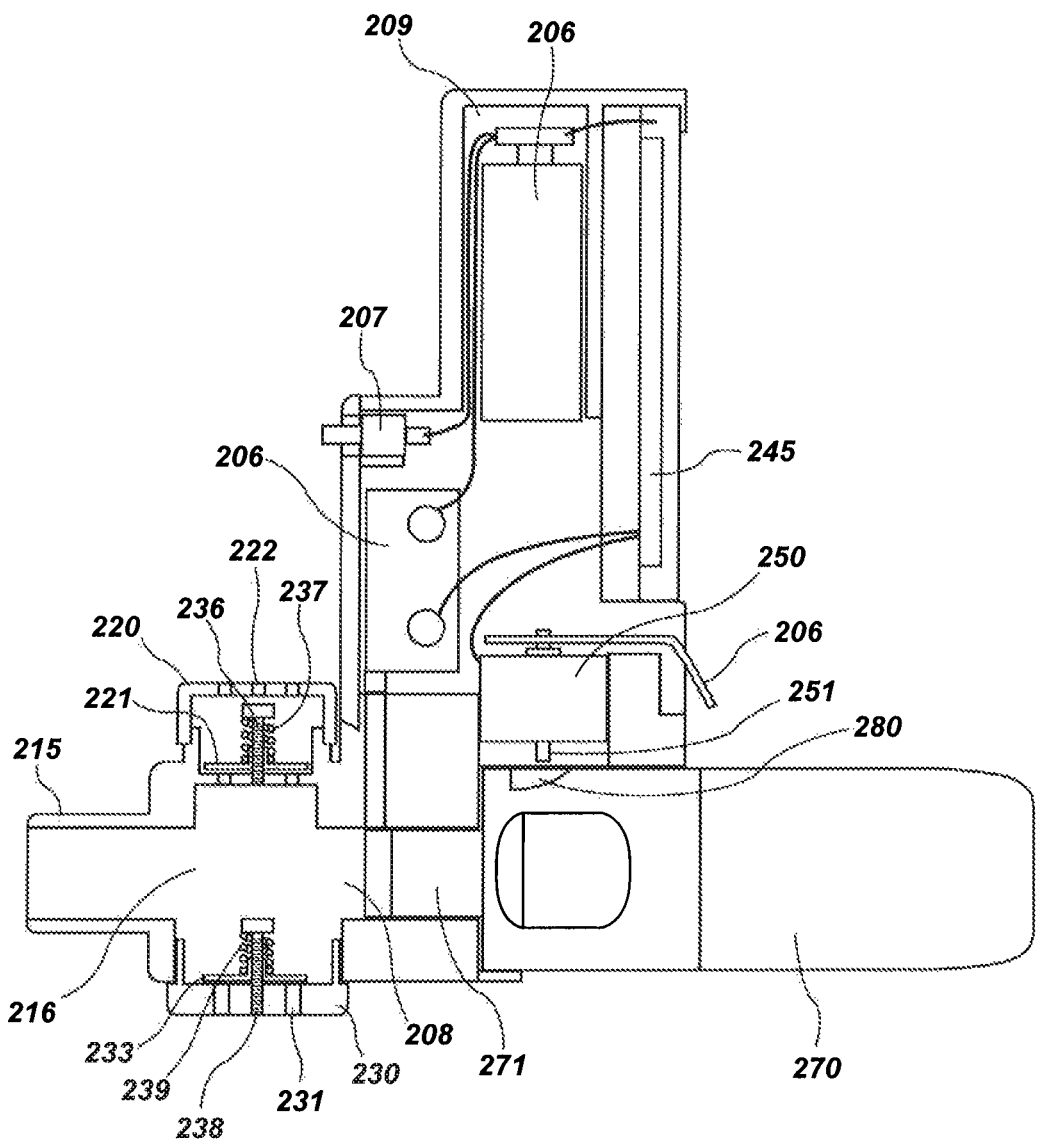
FIG. 11 is a cross-section side view of the inhalator device of FIG. 10.

With reference now to FIGS. 10 and 11, in accordance with one aspect of the invention, an inhalator device 200 is shown. Similar to the inhalator device 100, this device comprises a mouthpiece 215 having a primary chamber 216 with an inhale valve 230 disposed on a bottom portion of primary chamber 216. The inhale valve 230 comprises a plurality of apertures 231 leading from a bottom portion of the inhale valve 230 to a moveable plate 233. Plate 233 is disposed below an adjustable post 238 with a spring member 239 biasing the plate 233 against the top of apertures 231. The inhale valve 230 is biased in a normally closed position and is opened when negative pressure is induced within the primary chamber 216 of mouthpiece 215. In other words, the plate 233 of inhale valve 230 is moved upward when a user of the inhalator 200 inhales sufficiently to overcome the tension of spring 239 opening an airway permitting the ingress of air into the mouthpiece 215. The mouthpiece 215 comprises an oval 235 configured to be inserted into the mouth of a patient. The top of the mouthpiece 215 comprises a valve shown generally at 220. In one aspect of the invention, the valve 220 comprises a PEEP valve having a plurality of apertures 222 on the outside of the mouthpiece 215 and on a top of the valve 220. A plate 221 is disposed below an adjustable rod 236 and spring 237 assembly much like the inhale valve 230 on the bottom of the mouthpiece 215. In contrast to the inhale valve 230, the plate 221 of the PEEP valve 220 opens when the primary chamber 216 of the mouthpiece 215 experiences positive pressure. That is, when the user blows on the mouthpiece 215, plate 221 is directed upward against spring member 237 opening a passage between apertures 222 and the ambient air. The tension of spring member 237 may be selected in order to predetermine the quantity of pressure required to move the plate 221 upward sufficient to allow the passage of air. Both rods in the upper and lower valves may be threaded into a portion of the valve and therefore have an adjustable length. In this manner, the tension of the springs 237 and 239 may be adjusted.

A cavity is formed in the back of the housing 205 configured to receive a medicine cartridge 270 therein. In one aspect, medicine cartridge 270 comprises a cylindrical container with pressurized fluids therein. The distal end of the cartridge 270 comprises a valve 271. The valve 271 is operatively coupled to a button 280 on the side of the cartridge 270. When the device 200 is charged, a predetermined volume of medicine is disposed from the valve 271 when the button 280 is depressed. The valve 271 is in fluid communication with inlet 208 and, once connected to the mouthpiece 215, is also in fluid communication with primary chamber 216 of mouthpiece 215.

Inlet 208 of the housing 205 is also in fluid communication with pressure sensor 206. When a patient blows on the mouthpiece 215, the lower valve 230 closes and the upper PEEP valve 220 opens. Depending on the tension of spring 237 and the volume of air exhaled by the patient, an amount of positive pressure within the primary chamber 216 is created. Pressure sensor 206 is configured to detect the pressure within primary chamber 216 and the amount of time pressure is continuously maintained. The pressure sensor 206 is configured to relay a signal to circuit board 245 when a qualifying breath has been achieved. Pressure sensor 206 is configured with tolerances to relay signals when a pressure that falls within a predetermined range for the pre-determined period of time similar to those ranges discussed herein. The circuit board 245 is operatively coupled to motor 250. Motor 250 is positioned such that when the cartridge 270 is properly disposed within the rear of housing 205, a piston 251 disposed about the bottom of the motor 250 is positioned directly above the button 280. When activated, motor 250 drives piston 251 downward to dispense the medication.

A bypass trigger 252 is disposed on the back of the housing 205. The bypass trigger 252 is operatively coupled to piston 251 which activates the button 280. In this manner, in the event the device 200 does not fire as anticipated, or the patient is not capable of creating the prescribed pressure within the device 200 for the predetermined number of breaths or the predetermined amount of time, the patient may manually fire the device 200 by depressing the trigger 252 and administer medication. In one aspect of the invention, the housing 205 comprises a battery 206 operatively coupled to an on/off switch 207 and the circuit board 245. The housing 205 comprises a removable plate 208 accessing compartment 209 that contains the battery 206. A plurality of lights 211 are disposed on the side 210 of housing 205. As noted above, in one aspect of the invention, lights may be activated in any number of sequences to indicate that a qualifying breath has been achieved, that medication is being administered and an inhalation breath should be taken and held, and/or how long an inhalation breath should be held.

The devices and embodiments shown herein make reference to valves for inhalation and valves for exhalation. However, in one aspect of the invention only one valve is present restricting the exhalation flow out of the mouth of the patient through the chamber. In yet another embodiment, a two-way valve may be used that provides means for the ingress of ambient air into the chamber for patient inhalation and also provides means for restricting the exhalation flow out of the mouth of the patient. In another embodiment, the chamber does not have any valves. Rather, a volume of exhalation flow from the patient is restricted by placing a plurality of holes about the exterior of the mouthpiece or other location in the housing of the device in fluid communication with the mouthpiece. Like the embodiments described above, the amount of pressure required to activate the valve is adjustable as suits a particular application by valve design and/or sizing and number of holes placed in the mouthpiece.

A method of administering medication to a patient comprises providing a hand-held, portable inhalator device to the patient, the device comprising a mouthpiece comprising a chamber and a medication source in fluid communication with the chamber. The mouthpiece further comprises an aperture configured to permit egress of fluid out of the chamber. The device also comprises a trigger configured to dispense medication from the medication source into the chamber. The method further comprises placing the mouth of the patient about the mouthpiece and exhaling into the mouthpiece and out of the aperture for a predetermined period of time at a threshold level of positive pressure to achieve a qualifying breath and dispensing a quantity of medication into the chamber after the qualifying breath. In one aspect of the invention, the method further comprises dispensing the quantity of medication into the chamber after a plurality of qualifying breaths as suits a particular prescription or patient need. In another aspect, each qualifying breath comprises exhaling through the mouthpiece for between approximately 3 and 5 seconds at a pressure within the mouthpiece ranging from between approximately 2.8 cm to 3.2 cm H2O and the patient is provided with a visual or audible indicator when a qualifying breath has been achieved. In another aspect of the invention, contact between the mouth of the patient and the mouthpiece of the device is substantially constant between qualifying breaths.

In another aspect, a method of administering medication to a patient comprises placing an inhalator device into the mouth of a patient. The device comprises a mouthpiece comprising a chamber, a fluid outlet, and a fluid inlet. It also comprises a medication source in fluid communication with the chamber and a first valve disposed about the fluid inlet. The first valve is biased in a closed position and configured to open to permit the ingress of ambient air into the chamber when subject to a threshold level of negative pressure. A second valve is disposed about the fluid outlet and is biased in a closed position and configured to open when subject to a first threshold positive expiratory end pressure to permit egress of fluid from the chamber. A trigger is disposed on the device and configured to dispense medication into the chamber. The method further comprises exhaling through the mouthpiece for a threshold period of time at a second threshold level of positive pressure and dispensing a quantity of medication into the chamber after the second threshold level of positive pressure is maintained within the chamber for a threshold period of time.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

More specifically, while illustrative exemplary embodiments of the invention have been described herein, the present invention is not limited to these embodiments, but includes any and all embodiments having modifications, omissions, combinations (e.g., of aspects across various embodiments), adaptations and/or alterations as would be appreciated by those skilled in the art based on the foregoing detailed description. The limitations in the claims are to be interpreted broadly based on the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus-function are expressly recited in the description herein. Accordingly, the scope of the invention should be determined solely by the appended claims and their legal equivalents, rather than by the descriptions and examples given above.

The invention claimed is:

1. A hand-held, portable inhalator device, comprising:
a housing having a mouthpiece comprising a chamber operatively coupled to a medication inlet and a fluid outlet;
a valve operatively coupled to the fluid outlet, the valve configured to open when subjected to a first threshold level of positive pressure, the valve permitting egress of fluid from a chamber disposed about the housing;
a control circuit operatively coupled to a trigger, the trigger coupled to a medication source;
a pressure sensor operatively coupled to the chamber and the control circuit, the pressure sensor configured to detect a fluid pressure level within the chamber and transmit a signal to the control circuit after a qualifying breath has been detected, the qualifying breath comprising maintaining a second threshold level of positive pressure within the chamber for a threshold period of time;
wherein the control circuit is configured to activate the trigger only after receiving a plurality a signals from the pressure sensor indicating that a qualifying breath has been detected within the chamber for a predetermined period of times.

2. The inhalator device of claim 1, further comprising a second valve disposed about a fluid inlet, the second valve configured to open when subjected to a threshold negative pressure, the second valve permitting the ingress of ambient air into the chamber.

3. The inhalator device of claim 1, further comprising a pressure sensor disposed about the chamber configured to measure the pressure within the chamber.

4. The inhalator device of claim 1, further comprising a programmable logic controller coupled to the pressure sensor and the trigger, the controller programmed to activate a drive mechanism when the pressure sensor detects that the second threshold level of positive pressure has been achieved within the chamber for the threshold period of time.

5. The inhalator device of claim 1, further comprising a piston operatively coupled to and capable of activating a timing gear coupled to the trigger, the piston configured to activate the timing gear when a second threshold level of positive pressure has been achieved within the chamber for a threshold period of time.

6. The inhalator device of claim 1, wherein the trigger is configured to dispense medication after a second threshold level of positive pressure is achieved within the chamber of the mouthpiece, maintained for a threshold period of time within the mouthpiece, and the positive pressure drops to below a third positive pressure threshold.

7. A hand-held, portable inhalator device, comprising:
a housing containing a source of medication in fluid communication with a chamber of a mouthpiece, wherein the chamber comprises a fluid inlet configured to permit ingress of fluid external the housing into the chamber and a fluid outlet configured to permit egress of fluid out of the chamber;
a first valve disposed about the fluid outlet, wherein the first valve is biased in a closed position and configured to open when subject to a first threshold level of positive pressure;
a second valve disposed about the fluid inlet, wherein the second valve is biased in a closed position and is configured to open when subject to a threshold level of negative pressure within the chamber;
a control circuit operatively coupled to a trigger device, the trigger device disposed about the source of medication, the trigger device configured to dispense medication from the source of medication;
a pressure sensor operatively coupled to the chamber and the control circuit, the pressure sensor configured to detect a fluid pressure level within the chamber and transmit a signal to the control circuit after a qualifying breath has been detected, the qualifying breath comprising maintaining a second threshold level of positive pressure within the chamber for a threshold period of time;
wherein the control circuit is configured to activate the trigger device only after receiving a plurality of signals from the pressure sensor indicating that a qualifying breath has been detected within the chamber a predetermined number of times.

8. The inhalator device of claim 7, further comprising a sensor disposed about the mouthpiece configured to detect contact about the exterior of the mouthpiece.

9. The inhalator device of claim 8, wherein the control circuit is further configured to prevent activation of the trigger if contact about the exterior of the mouthpiece is not detected.

10. The inhalator device of claim 7, further comprising a plurality of lights, each light corresponding to detection of a qualifying breath.

11. The inhalator device of claim 7, further comprising a visual indicator that is activated when the predetermined number of qualifying breaths has been detected.

12. A portable inhalator device, comprising:
a chamber operatively coupled to a medication inlet and a fluid outlet;
a control circuit operatively coupled to a trigger, the trigger coupled to a medication source;
a pressure sensor operatively coupled to the chamber and the control circuit, the pressure sensor configured to detect a fluid pressure level within the chamber and transmit a signal to the control circuit after a qualifying breath has been detected, the qualifying breath comprising maintaining a threshold level of positive pressure within the chamber for a threshold period of time;

wherein the control circuit is configured to activate the trigger only after receiving a plurality a signals from the pressure sensor indicating that a qualifying breath has been detected within the chamber for a predetermined period of times.

13. The inhalator device of claim 12, wherein the threshold level of positive pressure ranges from approximately 2 cm to 4 cm H2O.

14. The inhalator device of claim 13, wherein the threshold period of time ranges from approximately 3 seconds to 5 seconds.

15. The inhalator device of claim 12, further comprising first and second valves operatively coupled to the chamber, the first value valve disposed about the fluid outlet, wherein the first valve is biased in a closed position and configured to open when subject to the first threshold level of positive pressure and wherein the second valve is biased in a closed position and is configured to open when subject to a threshold level of negative pressure within the chamber.

16. The device of claim 15, wherein the first and second valves are one-way valves.

17. The inhalator device of claim 12, further comprising a plurality of lights disposed about a portion of the device that are activated when a qualifying breath has been detected.

* * * * *